(12) United States Patent
Lee et al.

(10) Patent No.: US 9,976,003 B2
(45) Date of Patent: *May 22, 2018

(54) METHOD FOR PREPARING SUPER ABSORBENT POLYMER AND SUPER ABSORBENT POLYMER PREPARED THEREFROM

(71) Applicant: LG Chem, Ltd., Seoul (KR)

(72) Inventors: Yong Hun Lee, Daejeon (KR); Tae Bin Ahn, Daejeon (KR); Chang Sun Han, Daejeon (KR); Sung Jong Seo, Daejeon (KR)

(73) Assignee: LG Chem, Ltd. (KR)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/302,845

(22) PCT Filed: Nov. 9, 2015

(86) PCT No.: PCT/KR2015/012000
§ 371 (c)(1),
(2) Date: Oct. 7, 2016

(87) PCT Pub. No.: WO2016/085152
PCT Pub. Date: Jun. 2, 2016

(65) Prior Publication Data
US 2017/0029576 A1    Feb. 2, 2017

(30) Foreign Application Priority Data

Nov. 27, 2014  (KR) .................. 10-2014-0167735
Nov. 6, 2015   (KR) .................. 10-2015-0155892

(51) Int. Cl.
```
A61L 15/60      (2006.01)
C08F 2/10       (2006.01)
C08F 2/44       (2006.01)
C08F 220/06     (2006.01)
C08F 265/02     (2006.01)
C08F 285/00     (2006.01)
C08J 3/075      (2006.01)
C08J 3/24       (2006.01)
C08F 20/10      (2006.01)
C08F 220/10     (2006.01)
A61L 15/24      (2006.01)
C08F 265/04     (2006.01)
C08J 3/12       (2006.01)
C08F 2/48       (2006.01)
C08F 6/00       (2006.01)
C08F 290/06     (2006.01)
```

(52) U.S. Cl.
CPC .............. *C08J 3/245* (2013.01); *A61L 15/24* (2013.01); *A61L 15/60* (2013.01); *C08F 2/10* (2013.01); *C08F 2/48* (2013.01); *C08F 6/008* (2013.01); *C08F 20/10* (2013.01); *C08F 220/10* (2013.01); *C08F 265/02* (2013.01); *C08F 265/04* (2013.01); *C08F 285/00* (2013.01); *C08F 290/062* (2013.01); *C08J 3/075* (2013.01); *C08J 3/12* (2013.01); *C08J 3/24* (2013.01); *C08F 220/06* (2013.01); *C08J 2351/00* (2013.01)

(58) Field of Classification Search
CPC .... C08F 2/10; C08F 2/48; C08F 20/10; C08F 220/10; C08F 265/02; C08F 265/04; C08F 290/062; C08F 6/008; C08F 220/06; C08J 3/075; C08J 3/12; C08J 3/24; C08J 3/245; C08J 2351/00; A61L 15/24; A61L 15/60

See application file for complete search history.

(56) References Cited

U.S. PATENT DOCUMENTS

| | | | |
|---|---|---|---|
| 4,446,261 A | 5/1984 | Yamasaki et al. | |
| 4,771,105 A | 9/1988 | Shirai et al. | |
| 5,883,158 A | 3/1999 | Nambu et al. | |
| 6,391,451 B1 | 5/2002 | Mitchell et al. | |
| 7,781,551 B2 | 8/2010 | Pacetti et al. | |
| 9,700,873 B2 * | 7/2017 | Lee ..................... | C08F 2/10 |
| 2003/0014027 A1 | 1/2003 | Beihoffer et al. | |
| 2003/0219600 A1 | 11/2003 | Mitchell et al. | |
| 2005/0137546 A1 | 6/2005 | Joy et al. | |
| 2008/0234645 A1 | 9/2008 | Dodge et al. | |
| 2009/0131255 A1 | 5/2009 | Ikeuchi et al. | |

(Continued)

FOREIGN PATENT DOCUMENTS

| | | |
|---|---|---|
| CN | 1155250 A | 7/1997 |
| CN | 1226334 C | 11/2005 |

(Continued)

OTHER PUBLICATIONS

International Search Report from PCT/KR2015/012000, dated Mar. 21, 2016.
Odian, George, "Principles of Polymerization." Second Edition, John Wiley & Sons, Copyright 1981, p. 203.
Schwalm, Reinhold, "UV Coatings: Basics, Recent Developments and New Applications." Elsevier Science, Dec. 21, 2016, p. 115.
European Search Report for Application No. EP15863575 dated Jul. 24, 2017.

(Continued)

Primary Examiner — Irina S Zemel
Assistant Examiner — Jeffrey S Lenihan
(74) Attorney, Agent, or Firm — Lerner, David, Littenberg, Krumholz & Mentlik, LLP

(57) ABSTRACT

The present invention relates to a method for preparing a super absorbent polymer. The method for preparing a super absorbent polymer according to the present invention can provide a super absorbent resin exhibiting fast absorption rate and high saline flow conductivity while having excellent absorption properties such as a centrifuge retention capacity and an absorbency under pressure, by using the polycarboxylic acid-based copolymer under pulverization of the hydrous gel phase polymer.

8 Claims, No Drawings

(56) References Cited

U.S. PATENT DOCUMENTS

| | | |
|---|---|---|
| 2010/0099781 A1 | 4/2010 | Tian et al. |
| 2010/0100066 A1 | 4/2010 | Azad et al. |
| 2012/0309920 A1 | 12/2012 | Funk et al. |
| 2015/0175484 A1 | 6/2015 | Ko et al. |
| 2015/0197587 A1 | 7/2015 | Lee et al. |
| 2016/0280866 A1 | 9/2016 | Lee et al. |

FOREIGN PATENT DOCUMENTS

| | | |
|---|---|---|
| CN | 100443125 C | 12/2008 |
| CN | 101641064 A | 2/2010 |
| CN | 102197057 A | 9/2011 |
| EP | 0697217 A1 | 2/1996 |
| EP | 2340265 A1 | 7/2011 |
| JP | S56161408 A | 12/1981 |
| JP | S57158209 A | 9/1982 |
| JP | S57198714 A | 12/1982 |
| JP | H0696619 B2 | 11/1994 |
| JP | H09503954 A | 4/1997 |
| JP | H11140193 A | 5/1999 |
| JP | 2001220415 A | 8/2001 |
| JP | 2003534407 A | 11/2003 |
| JP | 2012505940 A | 3/2012 |
| KR | 940000965 B1 | 2/1994 |
| KR | 19990051876 A | 6/2000 |
| KR | 20010032226 A | 4/2001 |
| KR | 100371649 B1 | 5/2003 |
| KR | 20140025083 A | 3/2014 |
| KR | 20140063401 A | 5/2014 |
| KR | 20140133470 A | 11/2014 |
| WO | 2014077516 A1 | 5/2014 |
| WO | WO-2016085123 A1 * | 6/2016 |

OTHER PUBLICATIONS

Third Party Observation for PCT/KR2015/012000 submitted Feb. 9, 2017.
Third Party Observation for EP15863575.5 dated Feb. 17, 2017.

* cited by examiner

METHOD FOR PREPARING SUPER ABSORBENT POLYMER AND SUPER ABSORBENT POLYMER PREPARED THEREFROM

CROSS-REFERENCE TO RELATED APPLICATION(S)

This application is a national phase entry under 35 U.S.C. § 371 of International Application No. PCT/KR2015/012000, filed Nov. 9, 2015, which claims priority to Korean Patent Application No. 10-2014-0167735, filed Nov. 27, 2014 and Korean Patent Application No. 10-2015-0155892, filed Nov. 6, 2015, the disclosures of which are incorporated herein by reference.

TECHNICAL FIELD

The present invention relates to a method for preparing a super absorbent polymer which has fast absorption rate and high saline flow conductivity while having excellent absorption properties such as a centrifuge retention capacity and an absorbency under pressure.

BACKGROUND OF ART

Super absorbent polymer (SAP) is a synthetic polymer material capable of absorbing moisture from about 500 to about 1,000 times its own weight, and it has been also called a super absorbency material (SAM), an absorbent gel material (AGM) and so on. Such super absorbent polymers started to be practically applied in sanitary products, and now they are widely used for preparation of various products, for example, hygiene products such as disposable diapers for children, water retaining soil products for gardening, water stop materials for the civil engineering and construction, sheets for raising seedling, fresh-keeping agents for food distribution fields, or the like.

As a method for preparing such a super absorbent polymer, an inverse suspension polymerization method, an aqueous solution polymerization method or the like are known. Among them, the preparation of super absorbent polymers via inverse suspension polymerization is disclosed in Japanese Patent Publication Nos. Sho 56-161408, Sho 57-158209, Sho 57-198714, and so on. Furthermore, for the preparation of super absorbent polymers via aqueous solution polymerization, a thermal polymerization method of polymerizing a hydrous gel phase polymer while breaking and cooling the same in a kneader equipped with a plurality of spindles, and a photo-polymerization method of exposing a high-concentrated aqueous solution to UV rays or the like on a belt so as to carry out the polymerization and drying at the same time are known.

On the other hand, the absorption rate, one of important physical properties of super absorbent polymers is associated with the surface dryness of the product in contact with a skin, such as disposable diapers. In general, these absorption rates can be improved in a manner of widening a surface area of the super absorbent polymer.

As an example, a method of forming a porous structure on the particle surface of the super absorbent polymer by using a blowing agent has been applied. However, general blowing agents have a disadvantage that a sufficient amount of the porous structure cannot be formed and thus the absorption rate is not highly increased.

As another example, there is a method for increasing a surface area of the super absorbent polymer by reassembling fine particles obtained during preparation of the super absorbent polymer to form a porous particle with irregular shape. However, although the absorption rate of the super absorbent polymer can be improved through these methods, there is a limit that a centrifuge retention capacity (CRC) and an absorbency under pressure (AUP) of the polymer are relatively decreased. In this way, because physical properties such as an absorption rate, a centrifuge retention capacity, an absorbency under pressure of the super absorbent polymer have a trade-off relation, there is an urgent need for the preparation method capable of improving these properties simultaneously.

DETAILED DESCRIPTION OF THE INVENTION

Technical Problem

For resolving the aforesaid problems of the prior arts, it is an object of the present invention to provide a method for preparing a super absorbent polymer that has fast absorption rate and high permeability at the same time.

Technical Solution

To achieve the above object, the present invention provides a method for preparing a super absorbent polymer comprising the steps of:

1) carrying out thermal polymerization or photo-polymerization of a monomer composition comprising a water-soluble ethylene-based unsaturated monomer, a polymerization initiator and a polycarboxylic acid-based copolymer having a repeating unit represented by the following Chemical Formulas 1-a and 1-b to prepare a hydrous gel phase polymer;

2) drying the hydrous gel phase polymer;

3) pulverizing the dried polymer; and 4) surface-crosslinking the pulverized polymer:

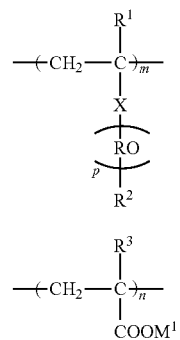

in Chemical Formulas 1-a and 1-b, $R^1$, $R^2$ and $R^3$ are each independently hydrogen, or an alkyl group having 1 to 6 carbon atoms, RO is an oxyalkylene group having 2 to 4 carbon atoms, $M^1$ is hydrogen, or a monovalent metal or non-metal on, X is —COO—, or an alkyloxy group having 1 to 5 carbon atoms or an alkyldioxy group having 1 to 5 carbon atoms, m is an integer of 1 to 100, n is an integer of 1 to 1000, and p is an integer of 1 to 150, provided that when p is 2 or more, two or more repeated —RO— may be the same or different from each other.

For the super absorbent polymer, a centrifuge retention capacity (CRC), an absorbency under pressure (AUP) and a saline flow conductivity (SFC) are evaluated as important physical properties, and especially, articles that super absorbent polymers are used, for example, disposable diapers and the like are thinned. Thus, having fast absorption rate and high saline flow conductivity at the same time is considered important. In order to increase the absorption rate, conventionally, a method for creating fine pores in a base polymer by addition of a chemical blowing agent that generates a gas when polymerizing super absorbent polymers, or a method for providing a porosity by applying addition of a physical force to the prepared hydrous gel phase polymer after the polymerization have been used. However, there are problems that it is difficult to significantly improve the absorption rate by using the chemical blowing agent, and the absorption properties are lowered by a method of simply applying a physical force to the hydrogel. In this way, because physical properties such as an absorption rate, a centrifuge retention capacity, an absorbency under pressure and a saline flow conductivity of the super absorbent polymer have a trade-off relation, there is an urgent need for the preparation method capable of improving these properties simultaneously.

Thus, in the present invention, by using the polycarboxylic acid-based copolymer under polymerization of the hydrous gel phase polymer, the polycarboxylic acid-based copolymer allows to reduce the internal crosslinking reaction rate, thereby providing a hydrous gel phase polymer which has uniform network structure and less water-soluble component. This also makes it possible to obtain fine particles which make a uniform pulverization and has a wide surface area when pulverizing the hydrous gel phase polymer.

The present invention will now be described in detail step by step.

Step of Preparing a Hydrous Gel Phase Polymer (Step 1)

First, the method for preparing the super absorbent polymer comprises a step of carrying out thermal polymerization or photo-polymerization of a monomer composition including a water-soluble ethylene-based unsaturated monomer, a polymerization initiator and a polycarboxylic acid-based copolymer to prepare a hydrous gel phase polymer.

Particularly, in the present invention, the polycarboxylic acid-based copolymer as defined above is used together. As an example, as the polycarboxylic acid-based copolymer, random copolymers derived from hydrophilic monomers such as alkoxy polyalkylene glycol mono(meth)acrylic acid ester-based monomer (as a representative example, methoxy polyethylene glycol monomethacrylate (MPEGMAA), etc.) and (meth)acrylic acid ester-based monomer (as a representative example, (meth)acrylic acid, etc.) can used, and these may be more advantageous for the expression of the effects described above.

Also, in order to better express the effects resulting from the addition of the polycarboxylic acid-based copolymer, the polycarboxylic acid-based copolymer has preferably a weight average molecular weight of 500 to 1,000,000.

Moreover, the content of the carboxylic acid-based copolymer may be appropriately adjusted depending on the kind and reaction conditions of the copolymer, and preferably it can be adjusted in the range of 0.001 to 5 parts by weight based on 100 parts by weight of the water-soluble ethylene-based unsaturated monomer. When the content of the polycarboxylic acid-based copolymer is excessively low, the above-described effects of the present invention may not be sufficiently exhibited. In contrast, when the content of the polycarboxylic acid-based copolymer is used excessively, functions inherent in the super absorbent polymer are lowered, and the absorption properties are reduced or it may result in a reduction in the surface tension or in the powder flow property, which is not preferable. More preferably, the content of the polycarboxylic acid-based copolymer is 0.01 parts by weight or more, 0.1 parts by weight or more, 0.2 parts by weight or more, or 0.3 parts by weight or more, and 4 parts by weight or less, 3 parts by weight or less, 2 parts by weight or less, or 1 part by weight or less, based on based on 100 parts by weight of the water-soluble ethylene-based unsaturated monomer.

The water-soluble ethylene-based unsaturated monomer included in the monomer composition may be any monomer that is generally used in the preparation of the super absorbent polymer. In a non-limiting example, the water-soluble ethylene-based unsaturated monomer may be a compound represented by the following Chemical Formula 3:

$$R_4\text{—COOM}^2 \qquad \text{[Chemical Formula 3]}$$

in Chemical Formula 3, $R_4$ is a $C_2$-$C_5$ alkyl group comprising an unsaturated bond, and $M^2$ is a hydrogen atom, a monovalent or divalent metal, an ammonium group, or an organic amine salt.

Preferably, the above-mentioned monomers may be one or more selected from the group consisting of acrylic acid, methacrylic acid, and monovalent or divalent metal salts of these acids, ammonium salts and organic amine salts. Thus, when using acrylic acid or a salt thereof as the water-soluble ethylene-based unsaturated monomer as described above, it is advantageous because the super absorbent polymer having improved water absorption properties can be obtained. In addition, as the monomers, maleic anhydride, fumalic acid, crotonic acid, itaconic acid, 2-acryloylethane sulfonic acid, 2-methacryloylethane sulfonic acid, 2-(meth)acryloylpropane sulfonic acid, or 2-(meth)acrylamide-2-methyl propane sulfonic acid, (meth)acrylamide, N-substituted (meth)acrylate, 2-hydroxyethyl(meth)acrylate, 2-hydroxypropyl(meth)acrylate, methoxypolyethyleneglycol (meth)acrylate, polyethyleneglycol(meth)acrylate, (N,N)-dimethylaminoethyl (meth)acrylate, (N,N)-dimethylaminopropyl(meth)acrylate, and the like may be used.

Here, the water-soluble ethylene-based unsaturated monomer may have an acidic group in which at least a part of the acidic group is neutralized. Preferably, the monomers that are used herein may include those partially neutralized with an alkaline substance such as sodium hydroxide, potassium hydroxide, or ammonium hydroxide.

In this case, the degree of neutralization of the monomer may be 40 to 95 mol %, or 40 to 80 mol %, or 45 to 75 mol %. The range of the degree of neutralization may vary depending on the final physical properties. However, if the degree of neutralization is too high, the neutralized monomer may be precipitated and thus it may be difficult to perform polymerization smoothly. In contrast, if the degree of neutralization is too low, the absorptive capacity of the polymer is greatly reduced and also it may exhibit elastic rubber-like properties which are difficult-to-handle.

Further, the concentration of the water-soluble ethylene based unsaturated monomer in the monomer composition may be appropriately controlled in consideration of a polymerization time, a reaction condition and the like, and it may be preferably 20 to 90% by weights or 40 to 65% by weights. Such concentration range may be advantageous to control the pulverizing efficiency during pulverization of the polymer which will be described later, while eliminating the necessity of removing non-reacted monomers after polymerization using a gel effect phenomenon that appears in the polymerization reaction of high-concentration aqueous solutions. However, if the concentration of the monomer is too low, the yield of the super absorbent polymer may be decreased. In contrast, if the concentration of the monomer is too high, there may be a process problem that a part of the monomers may be precipitated or pulverization efficiency may be lowered upon pulverization of the polymerized hydrous gel phase polymer, and physical properties of the super absorbent polymer may be degraded.

Meanwhile, the monomer composition may include a polymerization initiator that is generally used in the preparation of the super absorbent polymer. In a non-limiting example, the polymerization initiator that can be used herein includes a thermal polymerization initiator, a photo-polymerization initiator or the like, depending on the polymerization method. However, even in the case of using the photo-polymerization method, because a certain amount of heat is generated by the ultraviolet irradiation or the like and a certain degree of heat is generated according to the progress of the polymerization reaction, i.e., exothermic reaction, a thermal polymerization initiator may be additionally included Here, the photo-polymerization initiator, for example, may include one or more compounds selected from the group consisting of a benzoin ether, a dialkyl acetophenone, a hydroxyl alkylketone, a phenyl glyoxylate, a benzyl dimethyl ketal, an acyl phosphine, and α-aminoketone. Among them, specific examples of the acyl phosphine may include normal lucirin TPO, namely, 2,4,6-trimethyl-benzoyl-trimethyl phosphine oxide. More various photo-polymerization initiators are disclosed in "UV Coatings: Basics, Recent Developments and New Application (Elsevier, 2007), p 115," written by Reinhold Schwalm, which is incorporated herein by reference.

And, as the thermal polymerization initiator, one or more compounds selected from the group consisting of a persulfate-based initiator, an azo-based initiator, hydrogen peroxide, and ascorbic acid may be used. Specific examples of the persulfate-based initiator may include sodium persulfate ($Na_2S_2O_8$), potassium persulfate ($K_2S_2O_8$), ammonium persulfate (($NH_4)_2S_2O_8$), and the like. Also, examples of the azo-based initiator may include 2,2-azobis(2-amidinopropane)dihydrochloride, 2,2-azobis-(N,N-dimethylene)isobutyramidine dihydrochloride, 2-(carbamoylazo)isobutylonitrile, 2,2-azobis[2-(2-imidazolin-2-yl)propane] dihydrochloride, 4,4-azobis-(4-cyanovaleric acid) and the like. More various thermal polymerization initiators are disclosed in "Principle of Polymerization (Wiley, 1981), p 203" written by Odian, which is incorporated herein by reference.

These polymerization initiators may be included in the concentration of about 0.001% to 1% by weight based on the monomer composition. That is, when the concentration of the polymerization initiator is too low, it is not preferable because the polymerization rate may become slow and residual monomer in the final product can be extracted in a large amount. In contrast, when the concentration of the photo-polymerization initiator is too high, it is not preferable because physical properties of the polymer may be deteriorated, for example, the polymer chain forming a network is shortened, the content of water-soluble component is increased and the absorbency under pressure is lowered.

Meanwhile, the monomer composition may further include a crosslinking agent ("internal crosslinking agent") in order to improve physical properties of the polymer by the polymerization of the water-soluble ethylene-based unsaturated monomer. The crosslinking agent is for the internal crosslinking of the hydrous gel phase polymer and it can be used separately from a crosslinking agent for crosslinking the surface of the hydrous gel phase polymer ("surface crosslinking agent").

As the internal crosslinking agent, any compound can be used as long as it allows the formation of crosslinks during polymerization of the water-soluble ethylene-based unsaturated monomer.

In an non-limiting example of the internal crosslinking agents, polyfunctional crosslinking agents such as N,N'-methylenebisacrylamide, trimethylolpropane, tri(meth)acrylate, ethylene glycol di(meth)acrylate, polyethylene glycol (meth)acrylate, polypropylene glycol di(meth)acrylate, polypropylene glycol(meth)acrylate, butanediol di(meth)acrylate, butylene glycol di(meth)acrylate, diethylene glycol di(meth)acrylate, hexanedial di(meth)acrylate, triethylene glycol di(meth)acrylate, tripropylene glycol di(meth)acrylate, tetraethylene glycol di(meth)acrylate, dipentaerythritol pentaacrylate, glycerin tri(meth)acrylate, pentaerythritol tetraacrylate, triallylamine, ethylene glycol diglycidyl ether, propylene glycol, glycerin, or ethylene carbonate can be used alone, or two or more thereof can be used in combination, but are not limited thereto.

Such internal crosslinking agent may be included in the concentration of about 0.001% to 1% by weight based on the monomer composition. In other words, if the concentration of the internal crosslinking agent is too low, it is not preferable because the absorption rate of the polymer is lowered and the gel strength can be reduced. In contrast, if the concentration of the internal crosslinking agent is too high, the absorptive capacity is lowered and thus it may be not preferable as an absorber.

In addition, the monomer composition may further include additives such as a thickener, a plasticizer, a preservation stabilizer, an antioxidant, and so on, as needed.

Further, the monomer composition may be prepared in the form of a solution in which the raw materials such as the above-mentioned monomer, the polymerization initiator or the internal crosslinking agent are dissolved in a solvent.

In this case, as the solvent usable herein, any solvent can be used without limitation in the construction as long as it allows to dissolve the above-described raw materials. For example, as the solvent, water, ethanol, ethyleneglycol, diethyleneglycol, triethyleneglycol, 1,4-butanediol, propyleneglycol, ethyleneglycol monobutylether, propyleneglycol monomethylether, propyleneglycol monomethylether acetate, methylethylketone, acetone, methylamylketone, cyclohexanone, cyclopentanone, diethyleneglycol monomethylether, diethyleneglycol ethylether, toluene, xylene, butylolactone, carbitol, methylcellosolve acetate, N,N-dimethyl acetamide, or mixtures thereof may be used.

Further, the formation of the hydrous gel phase polymer through the polymerization of the monomer composition can be carried out by a conventional polymerization method, and the process thereof is not particularly limited. In a non-limiting example, the polymerization method is largely classified into a thermal polymerization and a photo-polymerization depending on the type of the polymerization energy source. The thermal polymerization may be carried out in a reactor like a kneader equipped with agitating spindles, and the photo-polymerization may be carried out in a reactor equipped with a movable conveyor belt.

As an example, the thermal polymerization can be carried out by injecting the monomer composition into a reactor such as a kneader equipped with the agitating spindles and then supplying hot air to the reactor or heating the reactor, thereby obtaining a hydrous gel phase polymer. The hydrous gel phase polymer discharged from the outlet of the reactor may be obtained as a particle having a size of centimeters or millimeters, depending on the type of the agitating spindles equipped in the reactor. Specifically, the hydrous gel phase polymer may be obtained into various shapes depending on the monomer concentration, the injection rate or the like of the monomer composition injected thereto, and the hydrous gel phase polymer having a (weight average) particle diameter of 2 mm to 50 mm can be generally obtained.

Further, as another example, when the photo-polymerization of the monomer composition is carried out in a reactor equipped with a movable conveyor belt, the hydrous gel phase polymer in the form of a sheet can be obtained. In this case, the thickness of the sheet may vary depending on the concentration and the injection rate of the monomer composition injected thereto. However, typically it is preferable to adjust to a thickness of 0.5 cm to 5 cm, in order to ensure the production speed or the like while allowing a uniform polymerization of the entire sheet.

The hydrous gel phase polymer obtained by the above-mentioned methods may have typically a moisture content of about 40% to about 80% by weight. As used here, the term "moisture content" refers to the content of moisture occupied based on total weight of the hydrous gel phase polymer, and it may be a value calculated by subtracting the weight of the dried polymer from the weight of the hydrous gel phase polymer. Specifically, it may be defined by the value calculated by measuring the weight loss according to evaporation of water in the polymer in the process of raising the temperature of the polymer and drying it through infrared heating. In this case, the drying condition is that the temperature is raised from the room temperature to about 180° C. and then maintained at 180° C., and thereby the total drying time can be set to 20 minutes including the temperature raising step for 5 minutes Step of Drying the Hydrous Gel Phase Polymer (Step 2)

Meanwhile, the method for preparing a super absorbent polymer comprises a step of drying the hydrous gel phase polymer formed through the aforementioned step.

Here, if necessary, to increase the efficiency of the drying step, a step of pulverizing (coarsely pulverizing) the hydrous gel phase polymer before the drying step can be further performed.

In an non-limiting example, a pulverizing device usable in the coarse pulverization may include a vertical pulverizer, a turbo cutter, a turbo grinder, a rotary cutter mill, a cutter mill, a disc mill, a shred crusher, a crusher, a chopper, a disc cutter and the like.

In this case, the coarse pulverization may be carried out so that the particle diameter of the hydrous gel phase polymer becomes 1 mm to 10 mm. In other words, in order to increase the drying efficiency, the hydrous gel phase polymer is preferably pulverized into a particle diameter of 10 mm or less. However, upon excessive pulverization, the aggregation phenomenon between particles may occur and thus, the hydrous gel phase polymer is preferably pulverized into a particle diameter of 1 mm or more.

Further, when the coarsely pulverizing step is carried out before the drying step of the hydrous gel phase polymer as described above, the hydrous gel phase polymer is in a state where moisture content is high and thus, a phenomenon where the polymer sticks to the surface of the pulverizer may occur. In order to minimize this phenomenon, in the coarsely pulverizing step, fine particle aggregation preventing agents such as steam, water, surfactant, clay or silica; thermal polymerization initiators such as persulfate-based initiators, azo-based initiators, hydrogen peroxide and ascorbic acid; epoxy-based crosslinking agents, diol crosslinking agents, crosslinking agents containing multi-functional groups of di-, tri- or higher functional groups, crosslinking agents such as a compound with mono-functional group including hydroxy group may be used as needed.

Meanwhile, the drying of the hydrous gel phase polymer immediately after the coarse pulverization or polymerization as described above may be carried out at a temperature of 120° C. to 250° C., or 150° C. to 200° C., or 160° C. to 180° C. (In this case, the above temperature can be defined as the temperature of a heating medium provided for drying or the internal temperature of drying reactors containing a heating medium and a polymer in the drying step). That is, if the drying temperature is low and the drying time is prolonged, the physical properties of the final polymer may be decreased. Thus, in order to prevent these problems, the drying temperature is preferably 120° C. or higher. Further, if the drying temperature is higher than necessary, only the surface of the hydrous gel phase polymer is dried, and thus a generation amount of fine powders may be increased during the pulverizing step to be described later and the physical properties of the final polymer may be deteriorated. Thus, in order to prevent these problems, the drying temperature is preferably 250° C. or less.

At this time, the drying time for the drying step is not particularly limited, but the drying time may be adjusted in the range of 20 minutes to 90 minutes at the above-mentioned drying temperature, in consideration of the process efficiency or the like, but it is not particularly limited thereto.

Further, in the drying step, any drying method may be used without limitation in the construction as long as it is generally known to be usable for the drying process of the hydrous gel phase polymer. Specifically, the drying step may be carried out by a method such as hot air supply, infrared irradiation, microwave irradiation or ultraviolet irradiation.

The polymer dried by the above-described method can exhibit a moisture content of about 0.1% to 10% by weight. In other words, if the moisture content of the polymer is less than 0.1% by weight, it may cause excessively drying and thus production costs may increase and the crosslinked polymer may degrade, which is not advantageous. In addition, if the moisture content is greater than 10% by weight, it is not preferable because a defect may occur in a subsequent step.

Step of Pulverizing the Dried Polymer (Step 3)

Meanwhile, the method for preparing a super absorbent polymer comprises a step of pulverizing the polymer dried through the aforementioned step.

The pulverizing step is a step for optimizing the surface area of the dried polymer, and it can be carried out so that the particle diameter of the pulverized polymer becomes 150 μm to 850 μm. Examples of a pulverizing device that can be used to pulverize into the above particle diameter may include a pin mill, a hammer mill, a screw mill, a roll mill, a disc mill, a jog mill or the like.

In addition, in order to control the physical properties of the super absorbent polymer powder finally manufactured, a step of selectively classifying particles having a particle diameter of 150 μm to 850 μm from the polymer powders obtained through the pulverizing step can be further carried out.

Step of Surface-Crosslinking the Pulverized Polymer (Step 4)

Meanwhile, the method for preparing a super absorbent polymer comprises a step of surface-crosslinking the polymer pulverized through the aforementioned steps.

The surface crosslinking is a step for increasing the crosslinking density near the surface of the polymer particles, and it can be carried out by a method of mixing a solution containing a crosslinking agent (surface crosslinking agent) with the pulverized polymer to perform crosslinking reaction.

Here, the kind of the crosslinking agent (surface crosslinking agent) contained in the surface cross-linking solution is not particularly limited. In a non-limiting example, the surface crosslinking agent may be one or more compounds selected from the group consisting of ethylene glycol diglycidyl ether, polyethylene glycol diglycidyl ether, glycerol polyglycidyl ether, propylene glycol diglycidyl ether, polypropylene glycol diglycidyl ether, ethylene carbonate, ethylene glycol, diethylene glycol, propylene glycol, triethylene glycol, tetraethylene glycol, propanediol, dipropylene glycol, polypropylene glycol, glycerin, polyglycerin, butanediol, heptanediol, hexanediol, trimethylolpropane, pentaerythritol, sorbitol, calcium hydroxide, magnesium hydroxide, aluminum hydroxide, iron hydroxide, calcium chloride, magnesium chloride, aluminum chloride, and iron chloride.

At this time, the amount of the surface crosslinking agent may be appropriately adjusted depending on the kind of the crosslinking agent or the reaction conditions, and preferably can be adjusted in the range of 0.001 to 5 parts by weight based on 100 parts by weight of the pulverized polymer. If the amount of the surface crosslinking agent is too low, the surface crosslink is not properly introduced and the physical properties of the final polymer can be reduced. In contrast, if the surface crosslinking agent is used in an excessively large amount, the absorptive capacity of the polymer may be lowered due to excessive surface crosslinking reaction, which is not desirable.

In the meantime, in order to carry out the surface crosslinking step, a method of adding the surface crosslinking solution and the pulverized polymer to a reaction tank and then mixing them, a method of spraying the surface crosslinking solution onto the pulverized polymer, a method of continuously supplying the pulverized polymer and the surface crosslinking solution to a mixer being continuously operated and then mixing them, and the like can be used.

Furthermore, when the surface crosslinking solution is added, water may be further added. Thus, by adding water together, more uniform dispersion of the crosslinking agent can be induced, the aggregation phenomenon of the polymer powder can be prevented, and the penetration depth of the surface crosslinking agent for the polymer powder can be more optimized. In consideration of these objects and advantages, the amount of water to be added can be adjusted in the range of 0.5 to 10 parts by weight relative to 100 parts by weight of the pulverized polymer.

Furthermore, the surface crosslinking step may be carried out at a temperature of 100° C. to 250° C., and it can be continuously made after the drying and pulverizing steps being conducted at a relatively high temperature. At this time, the surface crosslinking reaction can be carried out for 1 to 120 minutes, or 1 to 100 minutes, or 10 to 60 minutes. That is, in order to prevent the polymer particles from being damaged due to excessive surface reaction to lead to deterioration in the physical properties, while inducing surface crosslinking reaction to the minimum, the surface crosslinking can be carried out under the above-described reaction conditions.

By using these methods, a super absorbent polymer having less generation amount of coarse particles and fine particles, exhibiting fast absorption rate and high saline flow conductivity while having absorption properties such as a centrifuge retention capacity and an absorbency under pressure can be prepared.

Advantageous Effects

The method for preparing a super absorbent polymer according to the present invention can provide a super absorbent polymer exhibiting fast absorption rate and high saline flow conductivity while having excellent absorption properties such as a centrifuge retention capacity and an absorbency under pressure, by using the polycarboxylic acid-based copolymer under pulverization of the hydrous gel phase polymer.

DETAILED DESCRIPTION OF THE EMBODIMENTS

Hereinafter, the preferred Examples are provided for better understanding of the invention. However, these Examples are given for illustrative purposes only and not intended to limit the scope of the present invention.

Preparation Example 1

400 parts by weight of ion exchanged water was added to a 3 L four-neck flask reactor equipped with a stirrer, a thermometer, a nitrogen feeder and a circulating condenser, nitrogen was fed into the reactor while stirring, and the reactor was heated up to 75° C. under the nitrogen atmosphere.

Subsequently, 2 parts by weight of ammonium persulfate was added to the reactor and the resulting solution was completely dissolved. Then, an aqueous monomer solution prepared by mixing 600 parts by weight of methoxypolyethylene glycol monomethacrylate (average addition mole number of ethylene oxide (EO): about 50 moles), 96.6 parts by weight of methacrylic acid and 190 parts by weight of water, a mixed solution of 5 parts by weight of 3-mercaptopropionic acid and 5 parts by weight of water, and 150 parts by weight of a 3 wt % aqueous ammonium persulfate solution were continuously added to the reactor at a uniform speed for 4 hours. After completion of the addition, 5 parts by weight of a 3 wt % aqueous ammonium persulfate solution was added again thereto at a time.

Then, after raising the internal temperature of the reactor to 85° C., the reaction continued for 1 hour while maintaining the temperature at 85° C. to complete polymerization reaction.

The weight average molecular weight of the polycarboxylic acid-based copolymer thus prepared has a weight average molecular weight of 40,000, as measured by gel permeation chromatography (GPO).

Preparation Example 2

The polycarboxylic acid-based copolymer (weight average molecular weight: 40,000) was prepared in the same manner in Preparation Example 1, with the exception that it was neutralized with a 30 wt % aqueous triethanolamine solution for about 1 hours, after completion of the polymerization reaction as in Preparation Example 1.

Preparation Example 3

The polycarboxylic acid-based copolymer (weight average molecular weight: 40,000) was prepared in the same manner in Preparation Example 2, with the exception that it was neutralized with an aqueous sodium hydroxide solution instead of an aqueous triethanolamine solution.

Preparation Example 4

300 parts by weight of ion exchanged water was added to a 3 L four-neck flask reactor equipped with a stirrer, a thermometer, a nitrogen feeder and a circulating condenser, nitrogen was fed into the reactor while stirring, and the reactor was heated up to 75° C. under the nitrogen atmosphere.

Subsequently, 2 parts by weight of ammonium persulfate was added to the reactor and the resulting solution was completely dissolved. Then, an aqueous monomer solution prepared by mixing 300 parts by weight of methoxypolyethylene glycol monomethacrylate (average addition mole number of ethylene oxide (EO): about 50 moles), 49.8 parts by weight of methacrylic acid and 50 parts by weight of water, a mixed solution of 5 parts by weight of 3-mercaptopropionic acid and 30 parts by weight of water, and 80 parts by weight of a 3 wt % aqueous ammonium persulfate solution were continuously added to the reactor at a uniform speed for 4 hours. After completion of the addition, 5 parts by weight of a 3 wt % aqueous ammonium persulfate solution was added again thereto at a time.

Then, after raising the internal temperature of the reactor to 85° C., the reaction continued for 1 hour while maintaining the temperature at 85° C. to complete polymerization reaction.

The polycarboxylic acid-based copolymer thus prepared showed that it had a weight average molecular weight of 45,000, as measured by gel permeation chromatography (GPC).

Preparation Example 5

The polycarboxylic acid-based copolymer (weight average molecular weight: 45,000) was prepared in the same manner in Preparation Example 4, with the exception that it was neutralized with a 30 wt % aqueous triethanolamine solution for about 1 hours, after completion of the polymerization reaction as in Preparation Example 4.

Preparation Example 6

The polycarboxylic acid-based copolymer (weight average molecular weight: 45,000) was prepared in the same manner in Preparation Example 5, with the exception that it was neutralized with an aqueous sodium hydroxide solution instead of an aqueous triethanolamine solution.

Example 1

About 5 g of N,N'-methylene bisacrylamide as an internal crosslinking agent and 2 g of the polycarboxylic acid-based copolymer according to Preparation Example 1 were mixed with 500 g of acrylic acid to which about 971.4 g of 20% aqueous sodium hydroxide solution was added to prepare a monomer composition (neutralization degree of the acrylic acid-based monomer: 70 mol %).

The monomer composition was put in a 5 L tween-arm kneader having sigma-shaped spindles, and nitrogen gas was added for 30 minutes while maintaining the temperature at 65° C., thereby eliminating oxygen dissolved in the aqueous solution. 30.0 g of 0.2 wt % aqueous L-ascorbic acid solution, 50.5 g of aqueous sodium persulfate solution and 30.0 g of 2.0 wt % aqueous hydrogen peroxide solution were added thereto while stirring. Polymerization was initiated after 5 seconds, and the resulting gel was finely divided for 3 minutes by applying a shearing force of the twin-arm kneader. The divided hydrogel crosslinked polymer was removed from the kneader. The resulting hydrogel crosslinked polymer was put in a meat chopper (manufactured by SL Corporation, the discharge port with a mesh hole diameter of 10 mm) and divided to be less than 5 mm.

The finely divided gel was spread on a stainless wire gauze having a hole size of 600 μm to a thickness of about 30 mm, and dried in a hot air oven at 150° C. for 4 hours. The dried polymer thus obtained was pulverized by using a pulverizing device and then size-classified through a standard mesh sieve according to ASTM standard to obtain an absorbent polymer powder having a particle size of 150 to 850 μm.

Then, to 100 parts by weight of the polymer powder, a surface crosslinking solution containing 0.3 g of ethylene carbonate (surface crosslinking agent), 3 g of methanol and 3 g of water were added and uniformly mixed, and then dried in a hot air oven at 180° C. for 30 minutes. The dried powder was size-classified with a standard mesh sieve according to ASTM standard to obtain a super absorbent resin having a particle size of 150 μm to 850 μm.

Example 2

The super absorbent polymer was obtained in the same manner as in Example 1, with the exception that the polycarboxylic acid-based copolymer according to Preparation Example 2 instead of Preparation Example 1 was used.

Example 3

The super absorbent polymer was obtained in the same manner as in Example 1, with the exception that the polycarboxylic acid-based copolymer according to Preparation Example 3 instead of Preparation Example 1 was used.

Example 4

The super absorbent polymer was obtained in the same manner as in Example 1, with the exception that the polycarboxylic acid-based copolymer according to Preparation Example 4 instead of Preparation Example 1 was used.

Example 5

The super absorbent polymer was obtained in the same manner as in Example 1, with the exception that the polycarboxylic acid-based copolymer according to Preparation Example 5 instead of Preparation Example 1 was used.

Example 6

The super absorbent polymer was obtained in the same manner as in Example 1, with the exception that the polycarboxylic acid-based copolymer according to Preparation Example 6 instead of Preparation Example 1 was used.

Comparative Example 1

The super absorbent polymer was obtained in the same manner as in Example 1, with the exception that the polycarboxylic acid-based copolymer according to Preparation Example 1 was not added.

Comparative Example 2

The super absorbent polymer was obtained in the same manner as in Example 1, with the exception that polyethylene glycol (PEG-200) was added in the same amount, instead of the polycarboxylic acid-based copolymer according to Preparation Example 1.

Comparative Example 3

The super absorbent polymer was obtained in the same manner as in Example 1, with the exception that 1 g of sodium bicarbonate was added instead of the polycarboxylic acid-based copolymer according to Preparation Example 1.

Experimental Example 1

In order to evaluate the physical properties of the super absorbent polymers prepared in Examples and Comparative Examples, the following experiments were carried out and the results were shown in Table 1 below.

(1) CRC (Centrifuge Retention Capacity)

The centrifuge retention capacity of the absorbent polymer prepared in Examples and Comparative Examples was evaluated in accordance with the method EDANA WSP 241.2. That is, the polymers W (g) (about 0.2 g) obtained in Examples and Comparative Examples were uniformly put in a nonwoven fabric-made bag, followed by sealing. Then, the bag was immersed in a physiological saline solution (0.9 wt %) at room temperature. After a lapse of 30 minutes, water was removed from the bag using a centrifugal separator under conditions of 250 G for 3 minutes, and the weight W2 (g) of the bag was then measured. Further, the same procedure was carried out without using the polymer, and then the resultant weight W1 (g) was measured. Thus, CRC (g/g) was calculated from the respective weights thus obtained, according to the following Mathematical Formula.

$$CRC\ (g/g) = \{(W2-W1)/(W-1)\} \quad \text{[Mathematical Formula 1]}$$

(2) Absorbency Under Pressure (AUP)

The absorbency under pressure was measured for the absorbent polymers prepared in Examples and Comparative Examples in accordance with the method EDANA WSP 242.3. That is, a 400 mesh stainless steel net was installed in the cylindrical bottom of a plastic having an internal diameter of 60 mm. The absorbent polymer W (g) (about 0.90 g) was uniformly scattered on the steel net under conditions of room temperature and humidity of 50%, and a piston which can provide a load of 4.83 kPa (0.7 psi) uniformly was put thereon. The external diameter of the piston was slightly smaller than 60 mm, there was no gap between the cylindrical internal wall and the piston, and the jig-jog of the cylinder was not interrupted. At this time, the weight Wa (g) of the device was measured.

After putting a glass filter having a diameter of 90 mm and a thickness of 5 mm in a Petri dish having a diameter of 150 mm, a physiological saline solution composed of 0.90 wt % of sodium chloride was poured in the dish until the surface level became equal to the upper surface of the glass filter. A sheet of filter paper having a diameter of 90 mm was put thereon. The measuring device was put on the filter paper and the solution was absorbed under a load for about 1 hour. After 1 hour, the weight Wb (g) was measured after lifting the measuring device up. Thus, the absorbency under pressure (g/g) was calculated from the Wa and Wb, according to the following Mathematical Formula.

$$AUP\ (g/g) = \{Wb-Wa\}/W \quad \text{[Mathematical Formula 2]}$$

(3) Saline Flow Conductivity (SFC)

The saline flow conductivity was measured in accordance with the method disclosed in paragraphs [0184] to [0189] of Column 16 of U.S. patent application publication No. 2009-0131255.

(4) Vortex 50.0±1.0 mL of 0.9% NaCl solution was added to a 100 mL beaker. A cylindrical stirring bar (30×6 mm) was added thereto, and the above solution was stirred on the stirring plate at 600 rpm. 2.000±0.010 g of water absorbent polymer particles were added at a time to the beaker as quickly as possible. The stopwatch was started while starting the addition. The stopwatch was stopped when the surface of the mixture was in a "still" state. The above state means that the surface has no whirling. At this time, the mixture was still rotated, but the entire surface of the particles will be rotated as one unit. The time displayed on the stopwatch was recorded as a vortex time.

TABLE 1

| | CRC (g/g) | AUP (g/g) | SFC ($cm^3 \cdot sec \cdot 10^{-7}/g$) | Vortex (sec) |
|---|---|---|---|---|
| Example 1 | 30.6 | 24.8 | 53 | 47 |
| Example 2 | 30.6 | 25.0 | 52 | 47 |
| Example 3 | 30.5 | 25.0 | 55 | 48 |
| Example 4 | 30.6 | 24.8 | 51 | 46 |
| Example 5 | 30.5 | 24.7 | 50 | 48 |
| Example 6 | 30.5 | 24.9 | 52 | 46 |
| Comparative Example 1 | 30.5 | 24.5 | 46 | 60 |
| Comparative Example 2 | 30.8 | 24.4 | 44 | 56 |
| Comparative Example 3 | 30.2 | 23.9 | 39 | 48 |

As shown in Table 1, it was confirmed that the super absorbent polymers according to Examples had fast absorption rate and high saline flow conductivity (SFC) while exhibiting a centrifuge retention capacity and an absorbency under pressure equivalent to or higher than those of the super absorbent polymers according to Comparative Examples.

Meanwhile, in the case of using a hydrophilic polymer which was commercially available as in Comparative Example 2, the physical properties as in Examples had not been expressed, and even in the case of using a blowing agent which generates a gas under polymerization as in Comparative Example 3, the absorption rate and the saline flow conductivity were not satisfied at the same time. Accordingly, it could be confirmed that in accordance with the preparation method of the present invention, a super absorbent polymers having fast absorption rate and high saline flow conductivity at the same time could be prepared.

The invention claimed is:

1. A method for preparing a super absorbent polymer comprising the steps of:
   1) carrying out thermal polymerization or photo-polymerization of a monomer composition including a water-soluble ethylene-based unsaturated monomer, a polymerization initiator and a polycarboxylic acid-based copolymer having a repeating unit represented by the following Chemical Formulas 1-a and 1-b to prepare a hydrous gel phase polymer;
   2) drying the hydrous gel phase polymer;
   3) pulverizing the dried polymer; and
   4) surface-crosslinking the pulverized polymer;

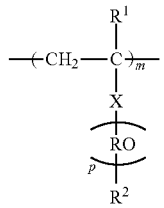

[Chemical Formula 1-a]

-continued

[Chemical Formula 1-b]

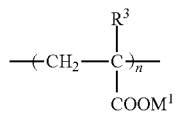

in Chemical Formulas 1-a and 1-b,
R$^1$, R$^2$ and R$^3$ are each independently hydrogen, or an alkyl group having 1 to 6 carbon atoms,
RO is an oxyalkylene group having 2 to 4 carbon atoms,
M$^1$ is hydrogen, or a monovalent metal or non-metal ion,
X is —COO—, or an alkyloxy group having 1 to 5 carbon atoms, or an alkyldioxy group having 1 to 5 carbon atoms,
m is an integer of 1 to 100,
n is an integer of 1 to 1000, and
p is an integer of 1 to 150, provided that when p is 2 or more, two or more repeated —RO— may be the same or different from each other.

2. The method for preparing a super absorbent polymer according to claim 1, wherein the polycarboxylic acid-based copolymer in the step 1 is mixed in an amount of 0.001 to 5 parts by weight based on 100 parts by weight of the water-soluble ethylene-based unsaturated monomer.

3. The method for preparing a super absorbent polymer according to claim 1, wherein the polycarboxylic acid-based copolymer has a weight average molecular weight of 500 to 1,000,000.

4. The method for preparing a super absorbent polymer according to claim 1, wherein the drying of the step 2 is carried out at a temperature of 120° C. to 250° C.

5. The method for preparing a super absorbent polymer according to claim 1, further comprising a step of pulverizing the hydrous gel phase polymer into a particle diameter of 1 mm to 10 mm, before the drying step of the hydrous gel phase polymer.

6. The method for preparing a super absorbent polymer according to claim 1, wherein the pulverization of the dried polymer is carried out so that the particle diameter of the pulverized polymer becomes 150 μm to 850 μm.

7. The method for preparing a super absorbent polymer according to claim 1, wherein the surface crosslinking is carried out at a temperature of 100 to 250° C.

8. The method for preparing a super absorbent polymer according to claim 1, wherein the surface crosslinking is carried out with one or more crosslinking agents selected from the group consisting of ethylene glycol diglycidyl ether, polyethylene glycol diglycidyl ether, glycerol polyglycidyl ether, propylene glycol diglycidyl ether, polypropylene glycol diglycidyl ether, ethylene carbonate, ethylene glycol, diethylene glycol, propylene glycol, triethylene glycol, tetraethylene glycol, propanediol, dipropylene glycol, polypropylene glycol, glycerin, polyglycerin, butanediol, heptanediol, hexanediol, trimethylolpropane, pentaerythritol, sorbitol, calcium hydroxide, magnesium hydroxide, aluminum hydroxide, iron hydroxide, calcium chloride, magnesium chloride, aluminum chloride, and iron chloride.

* * * * *